(12) United States Patent
Chow

(10) Patent No.: US 12,279,847 B2
(45) Date of Patent: Apr. 22, 2025

(54) STERILE CHANNEL PRE-DRAPE ASSEMBLY

(71) Applicant: INTUITIVE SURGICAL OPERATIONS, INC., Sunnyvale, CA (US)

(72) Inventor: Humphrey W. Chow, Cupertino, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 1034 days.

(21) Appl. No.: 16/185,113

(22) Filed: Nov. 9, 2018

(65) Prior Publication Data

US 2019/0142540 A1  May 16, 2019

Related U.S. Application Data

(60) Provisional application No. 62/584,445, filed on Nov. 10, 2017.

(51) Int. Cl.
*A61B 46/10* (2016.01)
*A61B 34/30* (2016.01)
*A61B 34/35* (2016.01)

(52) U.S. Cl.
CPC .............. *A61B 46/10* (2016.02); *A61B 34/35* (2016.02); *A61B 34/30* (2016.02)

(58) Field of Classification Search
CPC ......... A61B 46/00; A61B 46/10; A61B 46/40; Y10T 428/24; Y10T 428/24008; Y10T 428/31; B32B 1/00; B32B 1/04; B32B 3/00; B32B 3/02; B32B 2535/00

USPC .......... 128/849, 855; 428/80, 81, 98, 99, 409
See application file for complete search history.

(56) References Cited

U.S. PATENT DOCUMENTS

| | | | |
|---|---|---|---|
| 4,976,274 A | * | 12/1990 | Hanssen ................ A61B 46/00 128/849 |
| 6,671,581 B2 | | 12/2003 | Niemeyer et al. |
| 9,060,678 B2 | | 6/2015 | Larkin et al. |

(Continued)

FOREIGN PATENT DOCUMENTS

| | | | |
|---|---|---|---|
| WO | WO-2015142824 A1 * | 9/2015 | ............ A61B 34/30 |
| WO | WO-2018013300 A1 | 1/2018 | |

OTHER PUBLICATIONS

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

*Primary Examiner* — Maria V Ewald
*Assistant Examiner* — Ethan A. Utt
(74) *Attorney, Agent, or Firm* — Jones Robb, PLLC

(57) ABSTRACT

An apparatus includes a sterile channel pre-drape assembly comprising a plurality of legs radiating from a common center region. Each of the plurality of legs has one or more sterile interior surfaces and one or more outer surfaces. The sterile interior surfaces of a pair of the plurality of legs define a sterile channel that is bounded by the outer surfaces of the pair of the plurality of legs. The sterile channel pre-drape assembly also includes an attachment element affixed to the sterile channel pre-drape assembly. The attachment element is configured to attach the sterile channel pre-drape assembly to a portion of a surgical system.

14 Claims, 11 Drawing Sheets

(56) References Cited

U.S. PATENT DOCUMENTS

2004/0241216 A1\* 12/2004 Klun .................. A61L 15/24
  424/445
2011/0277776 A1   11/2011 McGrogan et al.
2016/0184037 A1    6/2016 Cooper et al.

\* cited by examiner

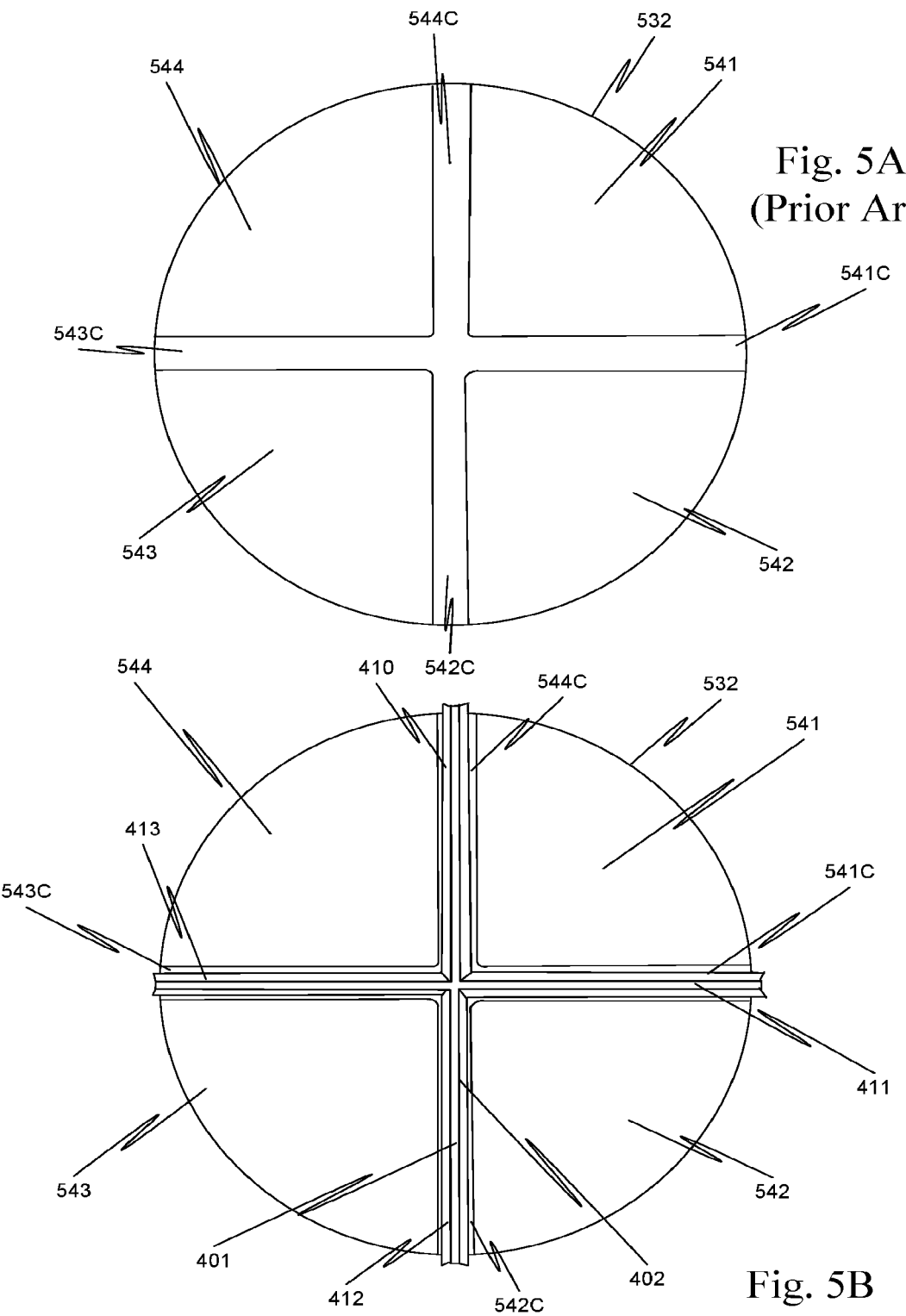

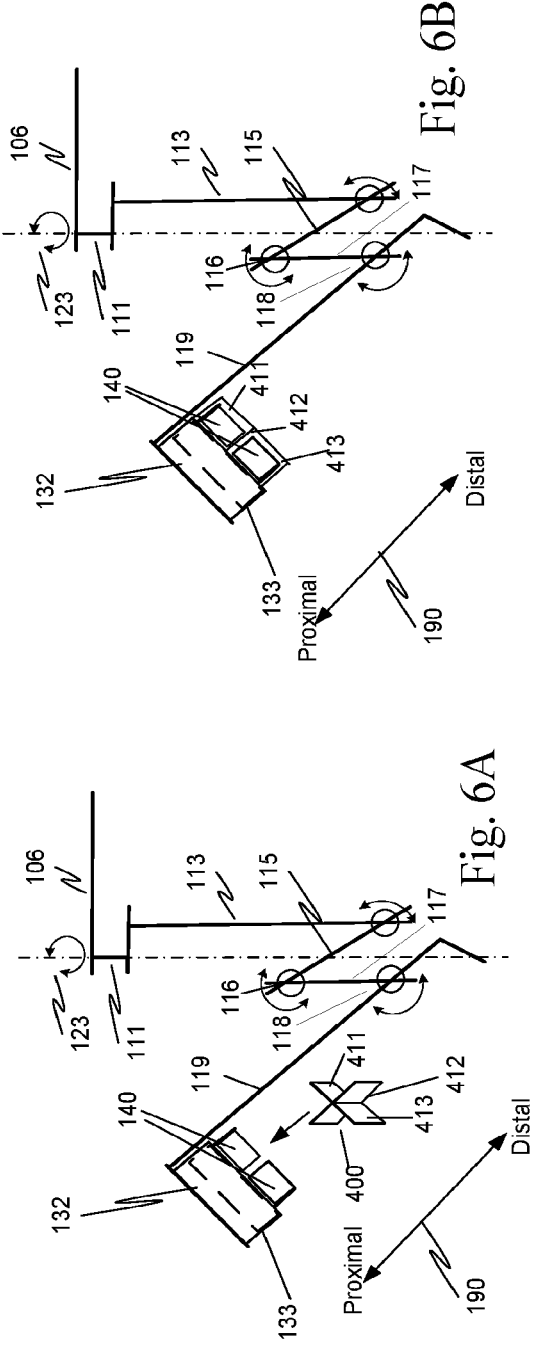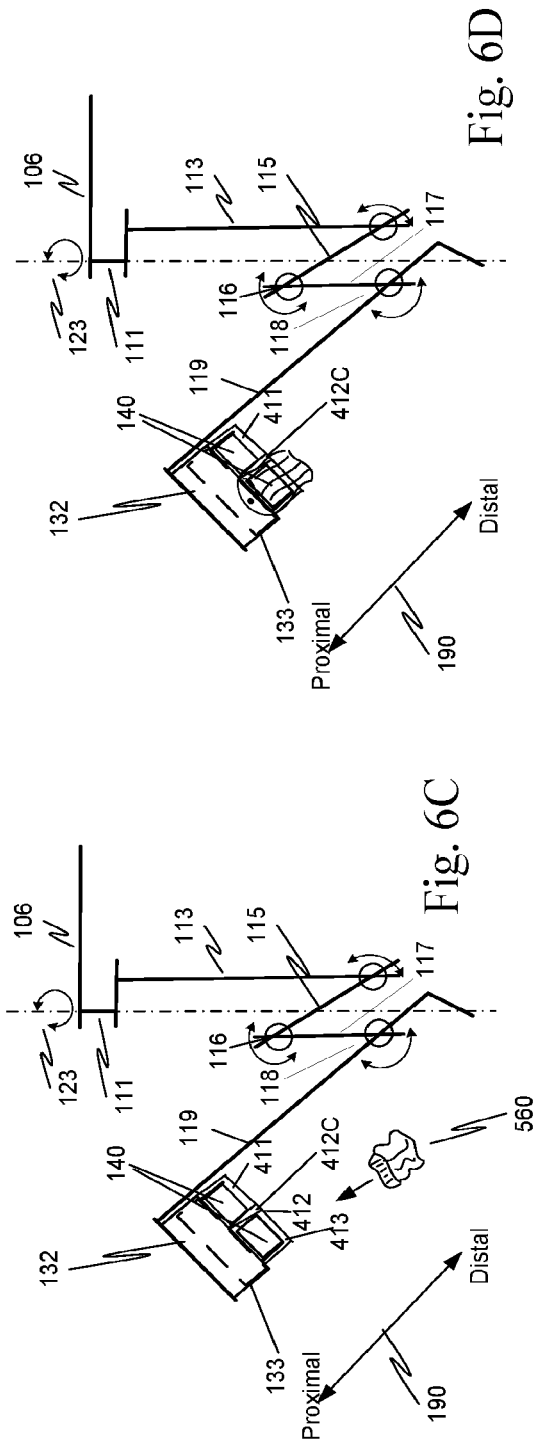

STERILE CHANNEL PRE-DRAPE ASSEMBLY

CROSS-REFERENCE TO RELATED APPLICATION

This application claims priority to U.S. Provisional Application No. 62/584,445 (filed Nov. 10, 2017), which is incorporated by reference herein in its entirety.

FIELD OF INVENTION

Aspects of the present invention relate generally to surgical drapes for computer-assisted surgical systems, and more particularly to mechanisms used during draping operation of the computer-assisted surgical system.

DESCRIPTION OF RELATED ART

A surgical drape has been previously used to cover a surgical manipulator such as plurality of surgical instrument manipulator assemblies 140 in computer-assisted surgical system 100. The drapes have taken various forms. In each instance, the manipulator and associated support links are covered with a surgical drape prior to the start of a surgical procedure.

Surgical system 100 is a computer-assisted teleoperated surgical system that includes an endoscopic imaging system 192, a surgeon's console 194 (master), and a patient side support system 110 (slave), all interconnected by wired (electrical or optical) or wireless connections 196. One or more electronic data processors may be variously located in these main components to provide system functionality. Examples are disclosed in U.S. Pat. No. 9,060,678 B2 (filed Jun. 13, 2007), which is incorporated by reference herein. In other embodiments, surgical systems optionally include a user interface (e.g., surgeon interface) directly connected or integrated with the patient side support system 110.

Imaging system 192 performs image processing functions on, e.g., captured endoscopic imaging data of the surgical site and/or preoperative or real time image data from other imaging systems external to the patient. Imaging system 192 outputs processed image data (e.g., images of the surgical site, as well as relevant control and patient information) to a surgeon at surgeon's console 194. In some aspects, the processed image data is output to an optional external monitor visible to other operating room personnel or to one or more locations remote from the operating room (e.g., a surgeon at another location may monitor the video; live feed video may be used for training; etc.).

Surgeon's console 194 includes multiple degrees-of-freedom ("DOF") mechanical input devices ("masters") that allow the surgeon to manipulate the instruments, entry guide(s), and imaging system devices, which are collectively referred to as slaves. These input devices may in some aspects provide haptic feedback from the instruments and surgical device assembly components to the surgeon. Console 194 also includes a stereoscopic video output display positioned such that images on the display are generally focused at a distance that corresponds to the surgeon's hands working behind/below the display screen. These aspects are discussed more fully in U.S. Pat. No. 6,671,581 (filed Jun. 5, 2002), which is incorporated by reference herein.

Control during insertion of the instruments may be accomplished, for example, by the surgeon moving the instruments presented in the image with one or both of the masters; the surgeon uses the masters to move the instrument in the image side to side and to pull the instrument towards the surgeon. The motion of the masters commands the imaging system and an associated surgical device assembly to steer towards a fixed center point on the output display and to advance inside the patient.

In one aspect, the camera control is designed to give the impression that the masters are fixed to the image so that the image moves in the same direction that the master handles are moved. This design causes the masters to be in the correct location to control the instruments when the surgeon exits from camera control, and consequently this design avoids the need to clutch (disengage), move, and declutch (engage) the masters back into position prior to beginning or resuming instrument control.

Base 101 of patient side support system 110 supports an arm assembly that includes a passive, uncontrolled setup arm assembly 120 and an actively controlled manipulator arm assembly 130. Actively controlled manipulator arm assembly 130 is referred to as entry guide manipulator 130.

In one example, setup arm assembly 120 includes two passive rotational setup joints 103 and 105. Rotational setup joints 103 and 105 allow manual positioning of coupled setup links 104 and 106 if the joint brakes for rotational setup joints 103 and 105 are released. Alternatively, some of these setup joints may be actively controlled, and more or fewer setup joints may be used in various configurations. Rotational setup joints 103 and 105 and setup links 104 and 106 allow a person to place entry guide manipulator 130 at various positions and orientations in Cartesian x, y, z space. A prismatic setup joint (not shown) between setup link 104 of setup arm assembly 120 and base 101 may be used for vertical adjustments 112.

A remote center of motion 146 is a location at which yaw, pitch, and roll axes intersect (i.e., the location at which the kinematic chain remains effectively stationary while joints move through their range of motion). Some of these actively controlled joints are manipulators that are associated with controlling DOFs of individual instruments, and others of these actively controlled joints are associated with controlling DOFs of a single assembly of these manipulators. The active joints and links are movable by motors or other actuators and receive movement control signals that are associated with master arm movements at surgeon's console 194.

As shown in FIG. 1, a manipulator assembly yaw joint 111, sometimes referred to as yaw joint 111, is coupled between an end of setup link 106 and a first end, e.g., a proximal end, of a first manipulator link 113, sometimes referred to as link 113. Yaw joint 111 allows first manipulator link 113 to move with reference to setup link 106 in a motion that may be arbitrarily defined as "yaw" around a manipulator assembly yaw axis 123. As shown, the rotational axis of yaw joint 111 is aligned with remote center of motion 146, which is generally the position at which an instrument enters the patient (e.g., at the umbilicus for abdominal surgery).

Setup link 106 is rotatable in a horizontal or x, y plane and yaw joint 111 is configured to allow first manipulator link 113 in entry guide manipulator 130 to rotate about yaw axis 123. Setup link 106, yaw joint 111, and first manipulator link 113 provide a constantly vertical yaw axis 123 for entry guide manipulator 130, as illustrated by the vertical line through yaw joint 111 to remote center of motion 146.

A distal end of first manipulator link 113 is coupled to a proximal end of a second manipulator link 115, sometimes referred to as link 115, by a first actively controlled rotational joint 114, sometimes referred to as rotational joint 114. A distal end of second manipulator link 115 is coupled to a proximal end of a third manipulator link 117, sometimes referred to as link 117, by a second actively controlled rotational joint 116. A distal end of third manipulator link 117 is coupled to a distal portion of a fourth manipulator link 119, sometimes referred to as link 119, by a third actively controlled rotational joint 118.

Links 115, 117, and 119 are coupled together to act as a coupled motion mechanism. Coupled motion mechanisms are well known (e.g., such mechanisms are known as parallel motion linkages when input and output link motions are kept parallel to each other). For example, if rotational joint 114 is actively rotated, rotational joints 116 and 118 are also actively rotated so that link 119 moves with a constant relationship to link 115. Therefore, it can be seen that the rotational axes of rotational joints 114, 116, and 118 are parallel. When these axes are perpendicular to rotational axis 123 of yaw joint 111, links 115, 117, and 119 move with reference to link 113 in a motion that may be arbitrarily defined as "pitch" around a manipulator assembly pitch axis.

The manipulator pitch axis extends into and out of the page in FIG. 1 at remote center of motion 146, in this aspect. The motion around the manipulator assembly pitch axis is represented by arrow 121. Since links 115, 117, and 119 move as a single assembly, first manipulator link 113 may be considered an active proximal manipulator link, and second through fourth manipulator links 115, 117, and 119 may be considered collectively an active distal manipulator link.

An entry guide manipulator assembly platform 132, sometimes referred to as platform 132, is coupled to a distal end of fourth manipulator link 119. An entry guide manipulator assembly 133 is rotatably mounted on platform 132. Entry guide manipulator assembly 133 includes an instrument manipulator positioning system.

Entry guide manipulator assembly 133 rotates plurality of surgical instrument manipulator assemblies 140 as a group around roll axis 125. Specifically, entry guide manipulator assembly 133 rotates as a single unit with reference to platform 132 in a motion that may be arbitrarily defined as "roll" around an entry guide manipulator assembly roll axis 125.

Each of a plurality of surgical instrument manipulator assemblies 140 is coupled to entry guide manipulator assembly 133 by a different insertion assembly 135. In one aspect, each insertion assembly 135 is a telescoping assembly that moves the corresponding surgical instrument manipulator assembly away from and towards entry guide manipulator assembly 133. In FIG. 1, each of the insertion assemblies is in a fully retracted position.

Each of the plurality of surgical instrument manipulator assemblies includes a plurality of motors that drive a plurality of outputs in an output interface of that surgical instrument manipulator assembly. See U.S. Patent Application Publication No. US 2016/0184037 A1 (filed Aug. 13, 2014), which is incorporated by reference, for one example of a surgical instrument manipulator assembly and a surgical instrument that can be coupled to the surgical instrument manipulator assembly.

In one aspect, a membrane interface that is part of a surgical drape may be placed between the instrument mount interface of a surgical instrument manipulator assembly and the input interface of the transmission unit of a corresponding surgical instrument. See, for example, U.S. Patent Application Publication No. US 2011/0277776 A1 (filed Aug. 12, 2010) for an example of the membrane interface and surgical drape. In another aspect, a sterile adapter that is part of a surgical drape may be placed between the instrument mount interface of the surgical instrument manipulator assembly and the input interface of the transmission unit of the corresponding surgical instrument. See, for example, U.S. Patent Application Publication No. US 2011/0277775 A1 (filed Aug. 12, 2010) for an example of a sterile adapter and a surgical drape.

FIG. 2 is a perspective view of a drape portion 200 of an extended surgical drape including a sterile adapter 250. Drape portion 200 includes a plurality of drape sleeves 205 coupled between rotatable seal 208 and sterile adapter 250.

Rotatable seal 208 operably couples proximal openings 203 of plurality of drape sleeves 205 to the manipulator platform of the manipulator arm assembly. In one example, rotatable seal 208 includes a rotatable labyrinth seal having a roll cover portion 208a and a base comb portion 208b. Base comb portion 208b is rotatable relative to roll cover portion 208a. Base comb portion 208b includes a disc with ribs 204 that form a plurality of wedge-shaped "frames" with apertures, each of the frames is sized to circumscribe a surgical instrument manipulator assembly. A proximal end of each of plurality of drape sleeves 205 is coupled to a different one of the plurality of wedge-shaped frames of base comb portion 208b. Ribbed base comb portion 208b aids in draping each individual one of the surgical instrument manipulator assemblies, which are closely clustered on the rotatable base plate of entry guide manipulator assembly 133, and further aids in maintaining the orientation and arrangement of each of the plurality of drape sleeves 205 as the draped surgical instrument manipulator assemblies move during a surgical procedure.

Although FIG. 2 illustrates each of plurality of drape sleeves 205 in an extended state, for example as the surgical instrument manipulator assemblies extend along their respective insertion mechanisms. Each of plurality of drape sleeves 205 may independently retract and extend as a corresponding surgical instrument manipulator assembly is independently and/or dependently controlled with respect to other surgical instrument manipulator assemblies.

Roll cover portion 208a fixedly mounts to frame of entry guide manipulator assembly platform 132 (e.g., the manipulator halo) and base comb portion 208b fixedly mounts to the rotatable base plate of entry guide manipulator assembly 133, such that when the rotatable base plate of entry guide manipulator assembly 133 is rotated, base comb portion 208b also rotates in combination with the draped surgical instrument manipulator assemblies. Since the proximal end of each of plurality of drape sleeves 205 is coupled to base comb portion 208b, all the plurality of drape sleeves 205 rotate together as a group with reference to a more proximal drape portion 210.

FIG. 3 is an illustration of another example of a sterile surgical drape 360 (FIG. 3), sometimes referred to as surgical drape 360 that can be used to drape part of computer-assisted surgical system 100. Sterile surgical drape 360 includes a first portion 361 and a second portion 362. Plurality of assemblies 366 for managing and retaining sterile surgical drape including a first assembly 367, a second assembly 368, and a third assembly 369 are affixed to first portion 361.

First portion 361 of sterile surgical drape 360 is connected to a stationary part of a rotatable seal 365, and second portion 362 is connected to a movable part of rotatable seal 365. In one aspect, rotatable seal 365 is labyrinth seal, where the stationary part is a roll cover portion of the labyrinth seal, and the movable part is a base comb portion of the labyrinth seal.

Second portion 362 of sterile surgical drape 360, in one aspect, includes a plurality of drape sleeves 362-1, 362-2, a plurality of boots 363-1, 363-2, and a plurality of mechanical interface elements 364-1 364-2. In one aspect, the plurality of mechanical interface elements are each a flexible membrane mechanical interface, such as that described in U.S. Patent Application Publication No. US 2011/0277776 A1. In another aspect, the plurality of mechanical interface elements are each a sterile adapter, such as that described in U.S. Patent Application Publication No. US 2011/0277775 A1.

Each of the plurality of mechanical interface elements 364-1 364-2 is coupled to a corresponding boot in plurality of boots 363-1, 363-2. Each of plurality of boots 363-1, 363-2 is coupled to a corresponding drape sleeve in plurality of drape sleeves 362-1, 362-2. An opening of each drape sleeve in plurality of drape sleeves 362-1, 362-2 is connected to the movable portion of rotatable seal 365, which, in one aspect, is a disc with ribs that form a plurality of wedge-shaped "frames" with apertures, each of the frames is sized to circumscribe a surgical instrument manipulator assembly. The open end of each of plurality of drape sleeves 362-1, 362-2 is coupled to a different one of the plurality of wedge-shaped frames. Each of plurality of boots 363-1, 363-2 fits around a surgical instrument manipulator assembly that is coupled by an insertion mechanism to an entry guide manipulator assembly 133 rotatably mounted on platform 132.

Plurality of assemblies 366 is used to configure surgical drape 360 on a portion of computer-assisted surgical system 100 so that the sterility of sterile portions of surgical drape 360 is not compromised. Sterile surgical drape 360 includes a sterile outer side—a first side—and an inner side—a second side, which is not treated as sterile. When surgical drape 360 is mounted on a part of a computer-assisted surgical system 100, the second side is against the part of the computer-assisted surgical system.

Typically, surgical drape 360 must be large enough to go around and cover the largest portion of computer-assisted surgical system 100 that is draped. This means that there is excess drape material when surgical drape 360 is fully deployed over at least some of the components of computer-assisted surgical system 100.

It is important that the sterile outside of the drape not contact any part of computer-assisted surgical system 100 during draping or operation of the computer-assisted surgical system 100, because this would contaminate the sterile side. Also, it is important that any excess drape material not be snagged or otherwise engaged with any portion of the computer-assisted surgical system during a surgical procedure because this could compromise the integrity of surgical drape 360. Plurality of assemblies 366 for managing and retaining sterile surgical drape help to solves these problems.

In the aspect illustrated in FIG. 3, plurality of assemblies 366 for managing and retaining sterile surgical drape includes a first assembly, a second assembly, and a third assembly. The first assembly is hinged cinch assembly 367, the second assembly is hinged cinch and attachment element assembly 368 (only partially visible), and the third assembly is an alignment and attachment element assembly 369 (only partially visible). The operation of these assemblies is described in International Patent Application Publication No. PCT/US2017/038350 (filed Jun. 20, 2017), which claims priority to U.S. Patent Application No. 62/362,194, both of which are incorporated herein by reference.

While each of the prior art drapes provides excellent protection of the draped apparatus, the manufacture and assembly of these drapes is complicated by the need to fuse together many different sleeves. Further, the bulk and size of a prior art drape complicates maintaining sterility of the drape during the draping process.

SUMMARY

A sterile channel pre-drape assembly, sometimes referred to as a pre-drape assembly, provides a simple and cost-effective way to enable draping co-located arms and/or co-located medical devices of a surgical system one at a time, and so eliminates the need for specialized parts and/or processes for combining drape sleeves and/or drape pockets into a single unified drape structure. The ability to drape co-located arms and/or co-located medical devices one at a time using single drape sleeves also simplifies the packing of the drape. In addition to facilitating individual draping of co-located medical devices, the sterile channel pre-drape assembly also protects sterile drape pockets and/or sterile drape sleeves from abrasion as the draped medical devices move within the sterile drape pockets, because a moving medical device contacts a surface of the sterile channel pre-drape assembly instead of the sterile drape pocket. Thus, the sterile channel pre-drape assembly could also be referred to as a sterile abrasion shield assembly.

In one aspect, an apparatus includes a sterile channel pre-drape assembly comprising a plurality of legs radiating from a common center region. Each of the plurality of legs has one or more sterile interior surfaces and one or more outer surfaces. The one or more sterile interior surfaces of a pair of the plurality of legs define a sterile channel that is bounded by the one or more outer surfaces of the pair of legs. In one aspect, one or more of the plurality of legs is flared between a first end and a second end of the leg.

The sterile channel pre-drape assembly also includes an attachment element affixed to the sterile channel pre-drape assembly. The attachment element is configured to attach the sterile channel pre-drape assembly to a portion of a surgical system.

In one aspect, the attachment element is affixed to a first end of the sterile channel pre-drape assembly. A second end of the sterile channel pre-drape assembly is open to facilitate passing a sterile drape sleeve through the sterile channel pre-drape assembly. The second end of the sterile channel pre-drape assembly is opposite from and removed from the first end of the sterile channel pre-drape assembly.

In yet another aspect, each pair of adjacent instrument manipulator assemblies of a plurality of instrument manipulator assemblies defines a channel between the pair of adjacent instrument manipulator assemblies. One or more of the plurality of legs of the sterile channel pre-drape assembly is configured to be positioned in the channel between the pair of adjacent instrument manipulator assemblies with an outer surface of the one or more legs being adjacent one of the pair of adjacent manipulator assemblies.

In this aspect, an attachment element affixed to the sterile channel pre-drape assembly is configured to attach the sterile channel pre-drape assembly to a main manipulator assembly. The main manipulator assembly is coupled to the plurality of instrument manipulator assemblies so that the plurality of instrument manipulator assemblies is co-located on the main manipulator assembly.

Also, in this aspect, the apparatus also includes a sterile instrument manipulator sleeve having a proximal end and a distal end. The proximal end includes one or more attachment elements configured to attach the sterile instrument manipulator sleeve to the main manipulator assembly. In some aspects, the sterile instrument manipulator sleeve includes one of an instrument sterile adapter attached to the distal end of the sterile instrument manipulator and a flexible membrane mechanical interface attached to the distal end of the sterile instrument manipulator sleeve.

In this aspect, the apparatus further comprises a sterile manipulator arm assembly drape having an open proximal end portion and an open distal end portion. One or more attachment elements are mounted on the proximal end portion of the sterile manipulator arm assembly drape. The attachment elements are configured to attach the proximal end of the sterile manipulator arm assembly drape to a proximal end of a manipulator arm assembly. A distal end of the manipulator arm assembly is attached to the main manipulator assembly.

In yet another aspect, a leg of the plurality of legs of the sterile channel pre-drape assembly is configured to be positioned in a channel between a pair of adjacent co-located medical devices with the outer surface of the leg adjacent one of the pair of adjacent co-located medical devices. The pair of adjacent co-located medical devices is included in a plurality of co-located medical devices.

The sterile channel pre-drape assembly includes an attachment element affixed to the sterile channel pre-drape assembly. The attachment element is configured to attach the sterile channel pre-drape assembly to a portion of a surgical system.

In one aspect, the attachment element is affixed to a first end of the sterile channel pre-drape assembly. A second end of the sterile channel pre-drape assembly is open to facilitate passing a sterile drape sleeve through the sterile channel pre-drape assembly. The second end of the sterile channel pre-drape assembly is opposite from and removed from the first end of the sterile channel pre-drape assembly.

This aspect of the apparatus also includes a sterile medical device sleeve having a proximal end and a distal end. The proximal end includes one or more attachment elements configured to affix the medical device sleeve to a portion of a surgical system. The sterile medical device sleeve is configured to drape one of the pair of adjacent co-located medical devices. Alternatively, the sterile medical device sleeve is configured to drape more than one of the co-located medical devices.

An assembly includes a structure configured to be mounted in one or more channels formed by spacings between adjacent medical devices in a plurality of co-located medical devices. The structure includes a plurality of legs. Each leg of the plurality of legs is configured to be inserted in one of the one or more channels. Also, each leg of the plurality of legs includes one or more exterior surfaces and one or more sterile interior surfaces. The one or more sterile interior surfaces of one or more legs of the plurality of legs create a sterile channel through which a sterile drape pocket can be passed without comprising sterility of the sterile drape pocket. In one aspect, the plurality of co-located medical devices is a plurality of surgical instrument manipulator assemblies. Also, in aspect, one or more of the plurality of legs is flared between a first end and a second end of the leg.

A method includes installing a sterile channel pre-drape assembly in channels formed by co-located medical devices of a surgical system. In a further aspect, the method also includes individually draping the co-located medical devices by passing a sterile medical device sleeve through a sterile channel formed by the sterile channel pre-drape assembly. The method repeats the individually draping of the co-located medical devices until all the co-located medical devices are draped. After all the co-located medical devices are draped, a link coupled to the co-located medical devices is draped.

BRIEF DESCRIPTION OF THE DRAWINGS

FIG. 5A is a schematic bottom view of a plurality of instrument manipulator assemblies co-located on a main manipulator assembly.

FIG. 5B is a schematic bottom view of the plurality of instrument manipulator assemblies co-located on a main manipulator assembly with the sterile channel pre-drape assembly of FIG. 4 installed.

FIGS. 6A to 6D illustrate draping of a plurality of medical devices co-located on a main assembly using the sterile channel pre-drape assembly of FIG. 4.

Figure 1:
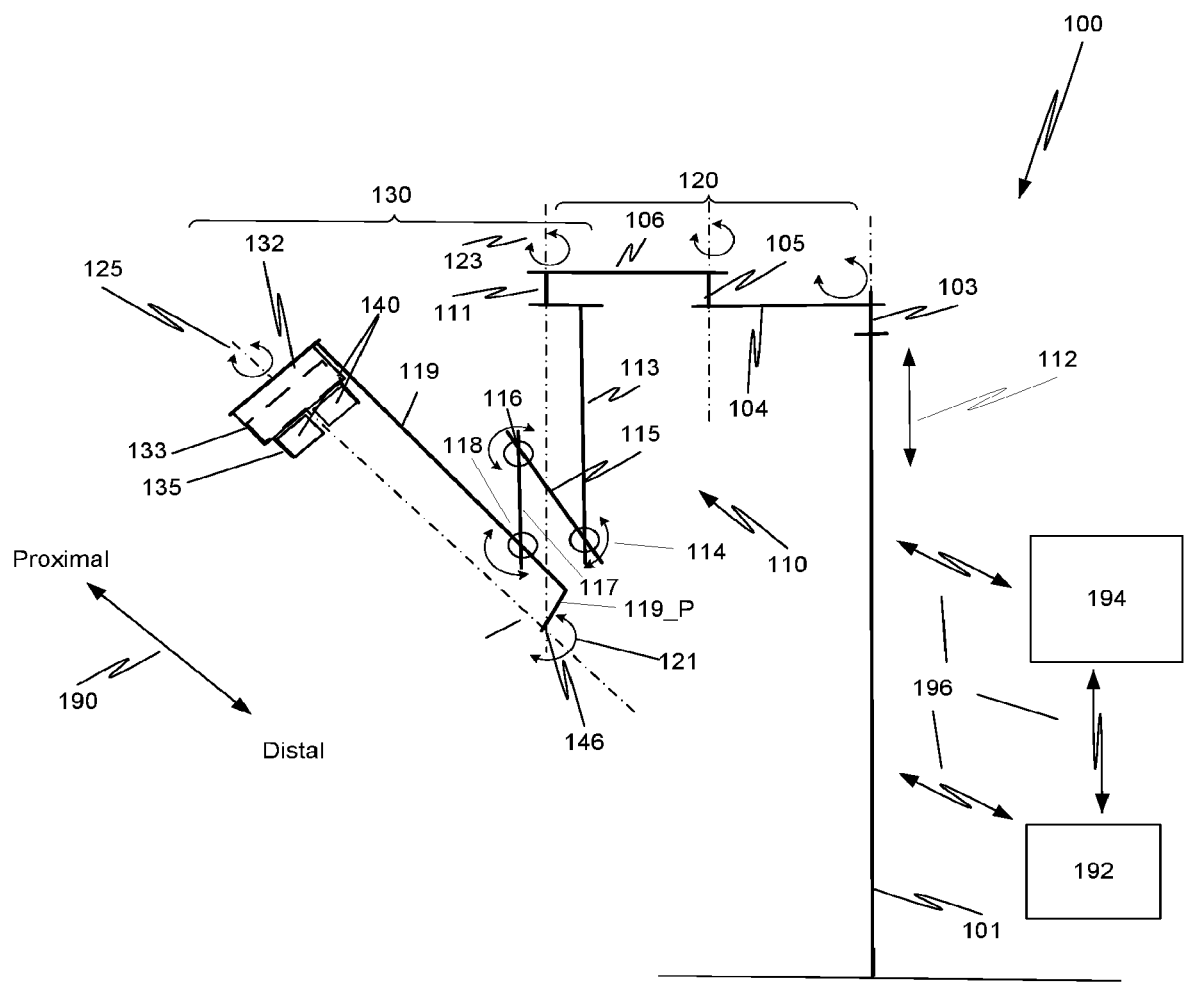
FIG. 1 is an illustration of a prior art computer-assisted teleoperated surgical system.
Figure 2:
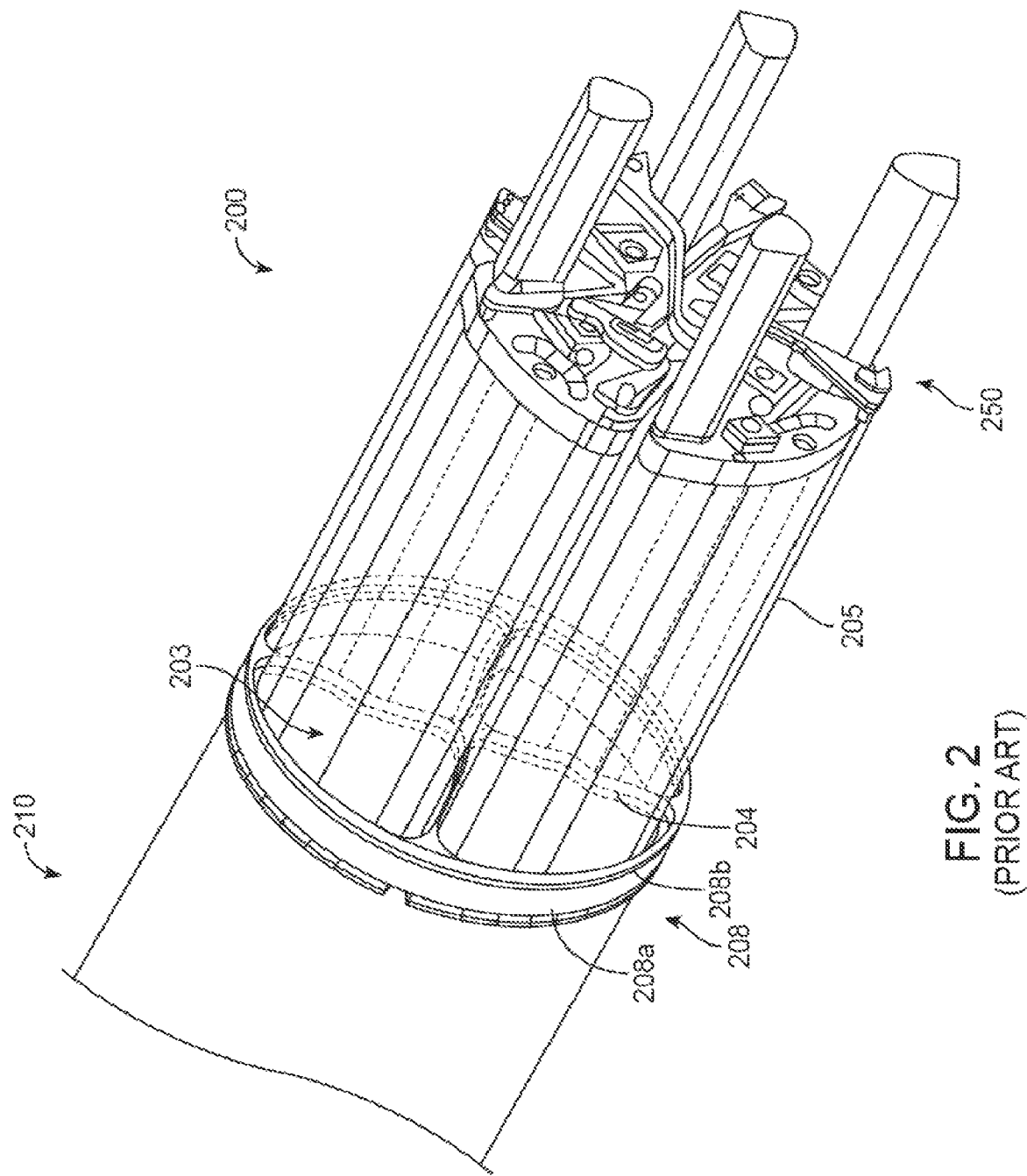
FIG. 2 is a representation of one example of a prior art surgical drape.
Figure 3:
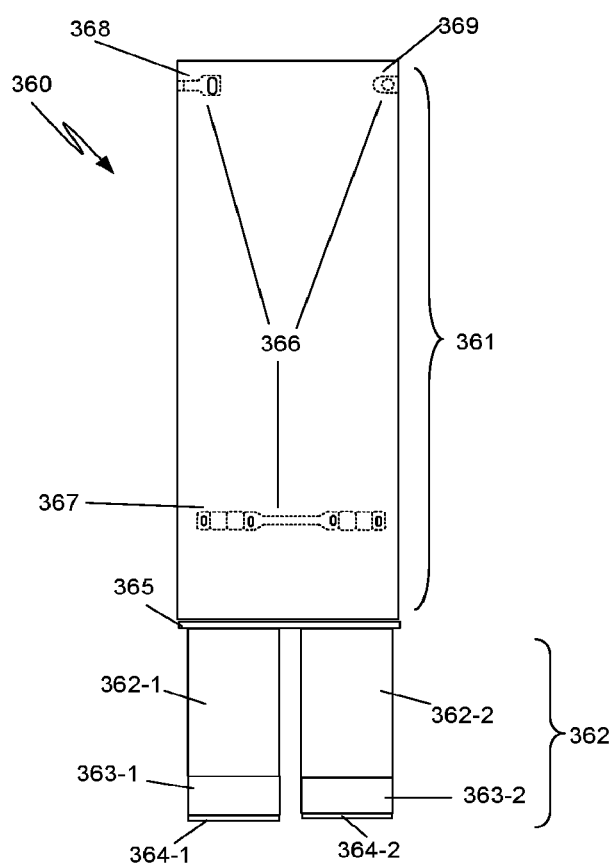
FIG. 3 is an example of a surgical drape that includes a plurality of assemblies for managing and retaining a sterile surgical drape on part of a surgical system.

In the drawings, the first digit in a three-digit reference numeral of an element is the number of the figure in which that element first appears and the first two digits in a four-digit reference numeral of an element is the number of the figure in which that element first appears.

DETAILED DESCRIPTION

In a surgical system (e.g., a computer-assisted teleoperated surgical system 100) medical device assemblies extending from a common platform, such as plurality of surgical instrument manipulator assemblies 140, need to be draped for use during a surgical procedure. However, the near proximity of non-sterile surfaces of the medical devices assemblies that can extend along the length and between the medical device assemblies means that it is not physically possible to sterily drape one medical device assembly at a time without compromising the sterility of the drape. As a result, the prior art drapes were designed such that a portion of the drape extends over all the medical device assemblies at once and then each of medical device assembly is advanced into a sterile sleeve extending from the portion of the drape that extends over all the medical device assemblies. However, such drapes can be costly to manufacture due to the need for specialized cuffs to combine sleeves together and such drapes require complex assembly and packaging processes that preclude the use of cost-reducing automation lines.

In one aspect, a sterile channel pre-drape assembly 400 (FIGS. 4A and 4B), sometimes referred to as pre-drape assembly 400, provides a simple and cost effective way to enable draping co-located arms and/or co-located medical devices one at a time, and so eliminates the need for specialized parts and/or processes for combining drape sleeves and/or drape pockets into a single unified drape structure. The ability to drape co-located arms and/or co-located medical devices individually one at a time using single drape sleeves also simplifies packaging.

Figure 4A:
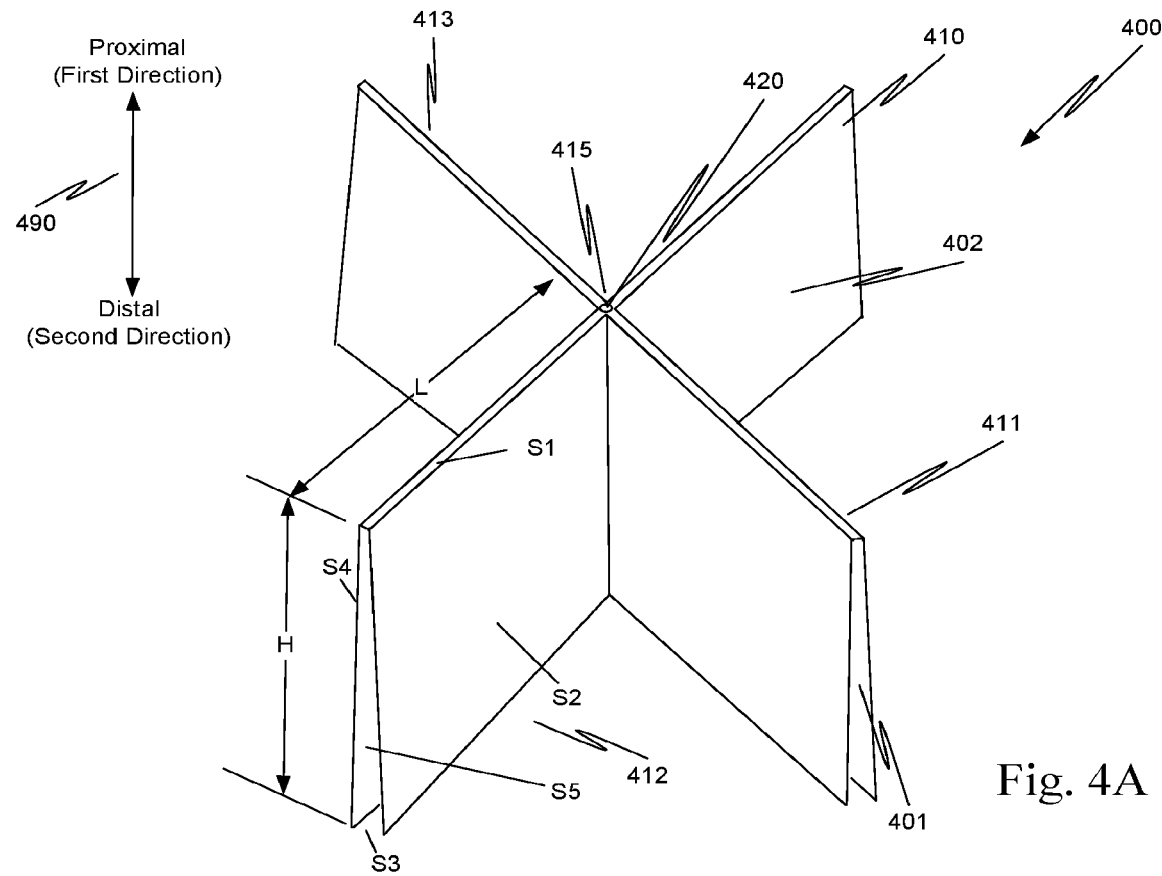
FIG. 4A is a perspective view of a one aspect of a sterile channel pre-drape assembly.
Figure 4B:
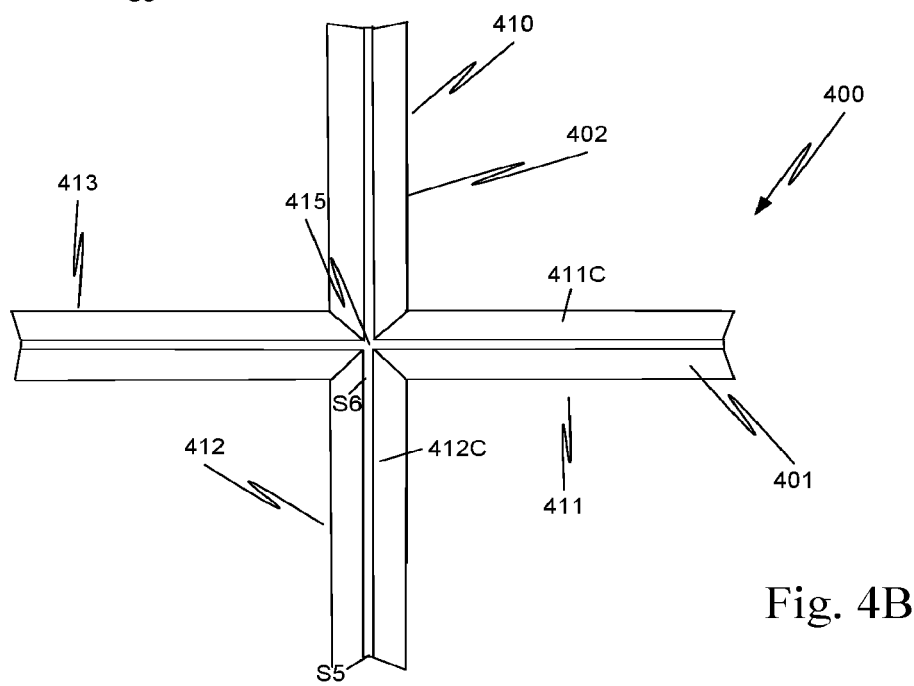
FIG. 4B is bottom view of the sterile channel pre-drape assembly of FIG. 4A.

FIG. 4A is a perspective view of one example of a sterile channel pre-drape assembly 400. FIG. 4B is a bottom view of sterile channel pre-drape assembly 400 of FIG. 4A.

Pre-drape assembly 400 includes a sterile inner side 401—a first side—and an outer side 402—a second side, which is not treated as sterile. When pre-drape assembly 400 is mounted between co-located parts of a surgical system, second side 402 is adjacent the co-located parts of the surgical system. Second side 402 protects the sterility of sterile inner side 401.

Sterile channel pre-drape assembly 400 includes a plurality of legs 410, 411, 412, 413 radiating from a common center region 415. Each of plurality of legs 410, 411, 412, 413 includes a portion of sterile inner side 401, sometimes referred to as sterile interior surface 401, and a portion of outer side 402, i.e., each of the plurality of legs includes one or more sterile interior surfaces and one or more outer surfaces. The one or more sterile interior surfaces of a leg make up a portion of sterile inner surface 401, while the one or more outer surfaces of a leg make up a portion of outer side 402. In this example, each leg includes six sides S1, S2, S3, S4, S5, S6 with three sides S3, S5, S6 of each of the plurality of legs being open to form a sterile channel, e.g., sterile channel 412C, bounded by the sterile inner surfaces of leg 412.

As explained more completely below, a sterile drape sleeve is passed through a sterile channel formed, for example, by the combination of sterile channels 411C, 412C and common center region 415. In this way a single sterile drape sleeve can be used to drape a single medical device without risking the sterility of the outer surface of the sterile drape sleeve. Sterile channels 411C, 412C prevent the sterile drape sleeve from contacting the non-sterile surfaces of the co-located parts of the surgical system.

In the example of FIGS. 4A and 4B, a leg is a three-dimensional trapezoidal structure. This is illustrative only and is not intended to be limiting. A leg could also have, for example, a three-dimensional structure with a triangular cross section, in which case, side S1 would be an edge, and in which case the leg would be flared out in the distal direction. Alternatively, a leg could be a three-dimensional structure with a rectangular cross section so that a leg is flared out in the distal direction. The shape of a leg is not critical so long as the functionality described more completely below is provided by the sterile channel pre-drape assembly. In general, a leg of a sterile channel pre-drape assembly has an outer surface and a corresponding sterile inner surface.

Also, in FIGS. 4A and 4B, each of plurality of legs 410, 411, 412, 413 is flared out as the leg extends from a first end of sterile channel pre-drape assembly 400 in a distal direction to a second end of sterile channel pre-drape assembly 400, e.g., as the leg extends along a lengthwise axis of sterile channel pre-drape assembly 400. While in this example, the flare extends between a first end and a second end of the leg, this is illustrative only and is not intended to be limiting. For example, the flare could extend in a proximal direction a predetermined distance from an open end—a distal end—of a leg so that the flare would not extend over a full height H of the leg.

Further, the flaring out of the legs along the lengthwise axis is illustrative only and is not intended to be limiting. In other aspects, each leg could have a wall that extends parallel to and adjacent an outer surface of a co-located part of a surgical system along the lengthwise axis of the sterile channel pre-drape assembly. In this aspect, the spacing between the inner surfaces of a leg would be maintained along the lengthwise axis so that a drape sleeve could easily be inserted into the sterile channel bounded by the inner surfaces of that leg.

In some aspects, sterile channel pre-drape assembly 400 is referred to as including a folded drape structure, because each of plurality of legs 410, 411, 412, 413 can viewed as a piece of material folded over to form the leg with at least three open sides. The exterior side, e.g., the combination of the exterior of sides S1, S2, and S4, of the folded piece of material protects the sterile interior surface of the folded piece of material. Thus, the exterior surface of the folded drape structure has a corresponding sterile inner surface, i.e., the inner surfaces of sides S1, S2, and S4, in this example. In some aspects, part of or all of side S1 also could be open so long as sterile channel pre-drape assembly 400 can be attached as described below.

Sterile channel pre-drape assembly 400 includes an attachment element 420, which is configured to affix pre-drape assembly 400 to a portion of a surgical system. Attachment element 420 is affixed to pre-drape assembly 400 on a first end, e.g., a proximal end, of pre-drape assembly 400, which in the example of FIGS. 4A and 4B is the proximal end of pre-drape assembly 400. Arrow 490 points in a proximal direction (an example of a first direction) and in a distal direction (an example of a second direction). A second end of the sterile channel pre-drape assembly 400, e.g., a distal end (sometimes referred to as a distal face), is open to facilitate passing a sterile drape sleeve into sterile channel pre-drape assembly 400. The second end of the sterile channel pre-drape assembly 400 is opposite from and removed from the first end of the sterile channel pre-drape assembly 400.

In some aspects, the pre-drape assembly 400 optionally comprises a material that is at least partially permeable, such as a membrane material with porous qualities, or a material that is substantially impermeable, such as a film. Exemplary materials for the pre-drape assembly and other draping components discussed herein, including sterile drape sleeves, include without limitation materials such as woven or non-woven polyurethane, polyethylene, thermoplastic polyurethane (TPU), or other materials. One example material, discussed further below, comprises flashspun polyurethane fibers and is available under the U.S. registered trademark TYVEK® of E. I. du Pont de Nemours and Comany and is referred to as TYVEK® material. Some non-limiting factors that can be considered when choosing a material include resistance of the material to shedding particles, thinness and flexibility of the material, and ability of the material to withstand various sterilization procedures.

Figure 5C:
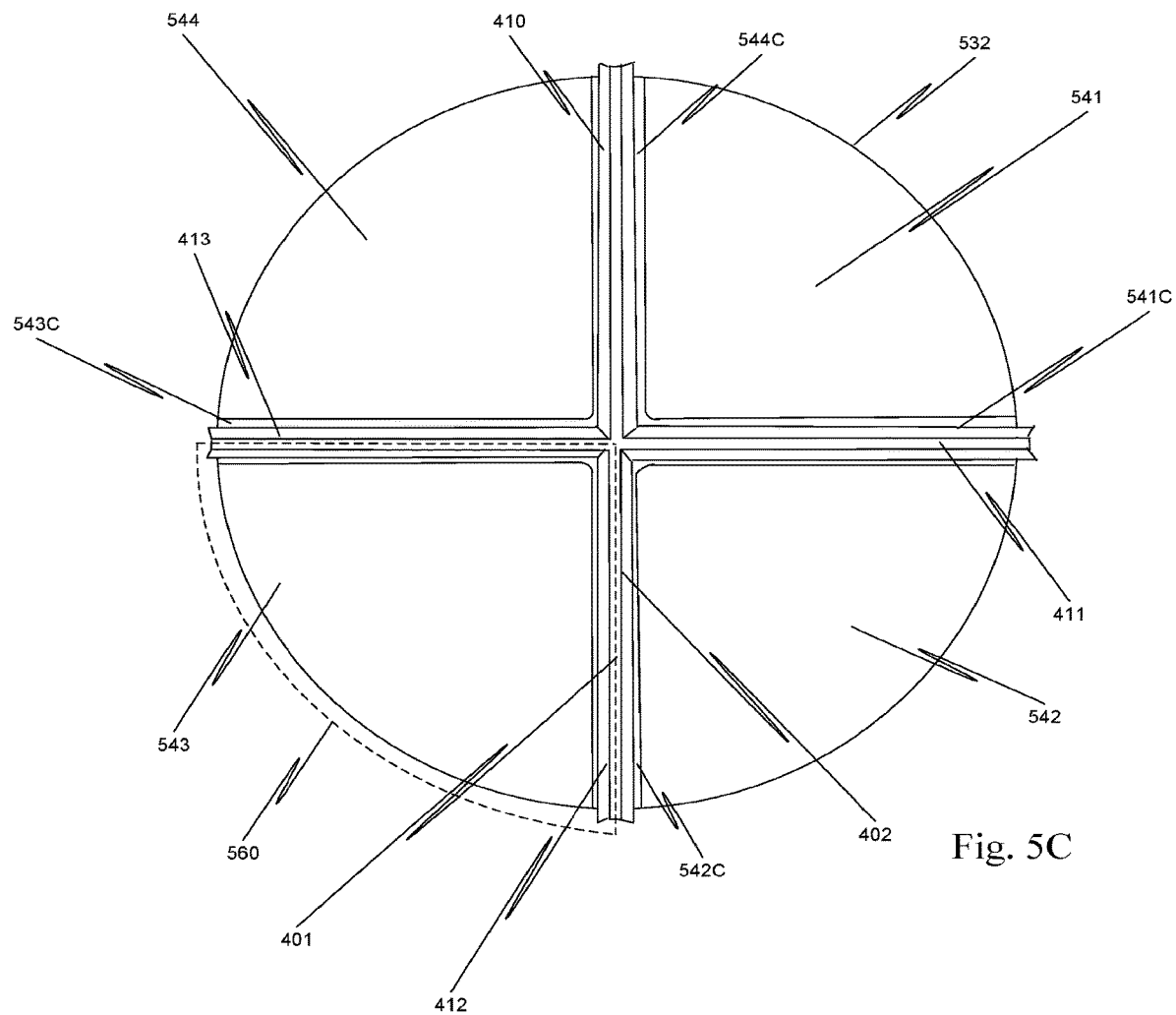
FIG. 5C is the schematic bottom view of FIG. 5B with a drape sleeve positioned in a sterile channel of the sterile channel pre-drape assembly.

FIG. 5A is a schematic bottom view of a plurality of instrument manipulator assemblies 541, 542, 543, 544 co-located on a main manipulator assembly 532. FIG. 5A is representative of a bottom view of entry guide manipulator assembly platform 132, entry guide manipulator assembly 133, and plurality of surgical instrument manipulator assemblies 140 in FIG. 1. Each pair (541, 542), (542, 543), (543, 544), (544, 541) of adjacent instrument manipulator assemblies of plurality of instrument manipulator assemblies 541, 542, 543, 544 defines a channel, e.g., channels 541C, 542C, 543C, 544C, between the pair of adjacent co-located instrument manipulator assemblies.

To insert pre-drape assembly 400 in channels 541C, 542C, 543C, 544C between co-located instrument manipulator assemblies 541, 542, 543, 544, pre-drape assembly 400 is positioned distal to instrument manipulator assemblies 541, 542, 543, 544 and then moved in the proximal direction towards co-located instrument manipulator assemblies 541, 542, 543, 544. See also FIG. 6A, which illustrates pre-drape assembly 400 in position to be inserted between plurality of co-located surgical instrument manipulator assemblies 140.

As pre-drape assembly 400 is moved in the proximal direction, each leg of pre-drape assembly 400 is aligned with a corresponding channel between instrument manipulator assemblies 541, 542, 543, 544. For example, leg 411 is aligned with channel 541C; leg 412 is aligned with channel 542C; leg 413 is aligned with channel 543C; and leg 410 is aligned with channel 544C.

In one aspect, a height H (FIG. 4A) of each of plurality of legs 410, 411, 412, 413 between a distal end of the leg and a proximal end of the leg (in the lengthwise direction) is selected to be longer than the corresponding length of an instrument manipulator assembly between a distal end and a proximal end of the instrument manipulator assembly. Similarly, a length L (FIG. 4A) of each of plurality of legs 410, 411, 412, 413 in the radial direction from common center region 415 to the end of the leg is selected to be longer than the corresponding radial length of an instrument manipulator assembly. The legs are designed to extend lengthwise and radially beyond the corresponding dimensions of the instrument manipulator assembly to allow sterile draping to occur without accidental contact with the non-sterile parts of the co-located instrument manipulator assemblies. This also provides abrasion resistance as the instrument manipulator assembly moves during use because the instrument manipulator assembly contacts the outside surface of a leg of the sterile channel pre-drape assembly instead of the drape sleeve itself. Hence, as noted elsewhere, sterile channel pre-drape assembly 400 could also be referred to as a sterile abrasion shield assembly.

Also, in this aspect, the length of the outer distal surface of pre-drape assembly 400 allows a user to grasp the distal outer surface and guide each leg of pre-drape assembly 400 into a corresponding channel between instrument manipulator assemblies 541, 542, 543, 544. Note that because outer side 402 is not considered sterile, it does not matter that outer side 402 is touched by a user, and does not matter if any part of outer side 402 of pre-drape assembly 400 contacts an instrument manipulator assembly. Since sterile inner side 401 is enclosed by outer side 402, the sterility of inner side 401 is maintained despite the user touching outer side 402 or despite outer side 402 contacting an instrument manipulator assembly.

Pre-drape assembly 400 is moved in the proximal direction until attachment element 420 is engaged and holds pre-drape assembly 400 in place. In one aspect, attachment element 420 is a metal disc that is held in an attachment receptacle on main manipulator assembly 532 by magnetism. However, any fixture commonly used to attach a sterile drape to a part of a surgical system could be used. For example, the pre-drape assembly 400 optionally can be attached to a drape portion already installed on a portion of the main manipulator assembly 532. As one example, the pre-drape assembly could be attached to a drape (not shown) installed over the manipulator assembly platform 132 (FIG. 6A), over one or more of manipulator links 113, 115, 117, and 119 (FIG. 6A), or over other portions of the surgical system.

In addition, in some aspects the pre-drape assembly 400 optionally can be provided with one or more additional devices to facilitate installation of the pre-drape assembly 400 on the main manipulator assembly 532. For example, a long, thin tool configured to slide between the instrument manipulator assemblies 541, 542, 543, 544 to assist a user in placing the legs 410, 411, 412, 413 between the instrument manipulator assemblies 541, 542, 543, 544 optionally can be provided with the pre-drape assembly 400.

FIG. 5B is a bottom view of pre-drape assembly 400 attached to main manipulator assembly 532 with each leg of pre-drape assembly positioned in one of the channels between a pair of co-located instrument manipulators. Similarly, FIG. 6B is an illustration of the legs of pre-drape assembly 400 installed between plurality of surgical instrument manipulator assemblies 140 of patient side support system 110. Notice that in FIG. 6B, the distal end of the legs of pre-drape assembly 400 extend in the distal direction beyond the distal faces of plurality of surgical instrument manipulator assemblies 140.

With pre-drape assembly 400 mounted, any one of plurality of co-located instrument manipulator assemblies 541, 542, 543, 544 can be individually draped with a drape sleeve without concern of damaging the drape sleeve and without concern of compromising the sterility of the drape sleeve.

To mount sleeve 560 around instrument manipulator assembly 543, sleeve 560 is positioned distal to instrument manipulator assembly 543. See FIG. 6C, where sleeve 560 is distal to surgical instrument manipulator assemblies 140. The exterior surface of sleeve 560 is sterile, but the interior surface of sleeve 560 is not treated as being sterile.

Sleeve 560 is moved in the proximal direction and is passed through a sterile channel formed by the sterile inner side 401 of pre-drape assembly 400, e.g., the interior surfaces of legs 412 and 413 combined with the interior of common center region 415. Since the interior walls of pre-drape assembly 400 are sterile, there is no problem with the sterile exterior surface of sleeve 560 contacting any interior portion of pre-drape assembly 400.

Legs 412 and 413 guide sleeve 560 around instrument manipulator 543 through channels 542C and 543C without risk of the exterior sterile surface of sleeve 560 contacting any of the co-located instrument manipulators. After sleeve 560 is positioned around instrument manipulator assembly 543, an attachment element in the proximal end of sleeve 560 is used to attach sleeve 560 to a portion of main manipulator assembly 532 that rotates plurality of instrument manipulator assemblies 541, 542, 543, 544 as a group. See FIG. 6D.

In the example of FIG. 5D, each instrument manipulator assembly was draped individually. However, in some configurations of plurality of instrument manipulator assemblies 541, 542, 543, 544, it may be possible to drape more than one instrument manipulator assembly using a single drape sleeve, e.g., two of the instrument manipulator assemblies are coupled so that the two assemblies move together.

For example, if a single drape sleeve were used to drape instrument manipulator assemblies 543 and 544, the drape sleeve 560 would be moved in the proximal direction and passed through a sterile channel formed by the sterile inner side 401 of pre-drape assembly 400, e.g., the interior surfaces of legs 412 and 410 combined with the interior of common center region 415. Sterile channel pre-drape assembly 400 provides a sterile channel for draping any subset of plurality of instrument manipulator assemblies 541, 542, 543, 544 with a single drape sleeve.

In the above description of the process flow for installing the pre-drape and drape sleeves, the pre-drape assembly 400 is installed on the main manipulator assembly 532, and the sleeve 560 is then installed over one or more of the instrument manipulator assemblies 541, 542, 543, 544. In other aspects, the pre-drape assembly 400 optionally can be assembled with one or more drape sleeves (such as sleeve 560) prior to installation on the main manipulator assembly 532, after which the combined assembly of pre-drape 400 and sleeves can be installed over the main manipulator assembly 532.

Further, the pre-drape assembly 400 optionally can be provided as multiple separate pre-drape components that can be assembled together prior to, or at the same time as, installation on the main manipulator assembly 532. For example, a pre-drape assembly could include two or more separate components, each configured to be individually inserted within one or more of the channels 541C, 542C, 543C, 544C. For example, the four legs 410, 411, 412, and 413 of the pre-drape assembly 400 can each optionally comprise a separate component, and each of the separate components can be assembled together to form the pre-drape assembly 400. In other aspects, the pre-drape assembly 400 optionally can comprise two, three, or more separate components that can be assembled to form the pre-drape assembly 400. For example, opposing legs 410 and 412, or 411 and 413, can be a single piece, and the other of opposing legs 410 and 412, or 411 and 413, can be formed by one or more separate components to form the pre-drape assembly 400. Additionally, while the above description describes installing the pre-drape assembly 400 by moving the pre-drape assembly in the proximal direction from a distal position, optionally the pre-drape assembly 400 can be installed within each channel 541C, 542C, 543C, 544C by moving the pre-drape assembly (or each pre-drape component) into each channel from the side, i.e., in a direction aligned with the respective channel and perpendicular to the proximal-distal direction shown in the drawings.

In the above examples, four co-located devices were considered. However, this is illustrative only and is not intended to be limiting. The sterile channel pre-drape assembly can be used with any number of co-located devices with the number of legs of the pre-drape assembly being equal to the number of co-located devices. Examples of some other aspects of the sterile channel pre-drape assembly are presented in FIGS. 7A and 7B.

Figure 7A:
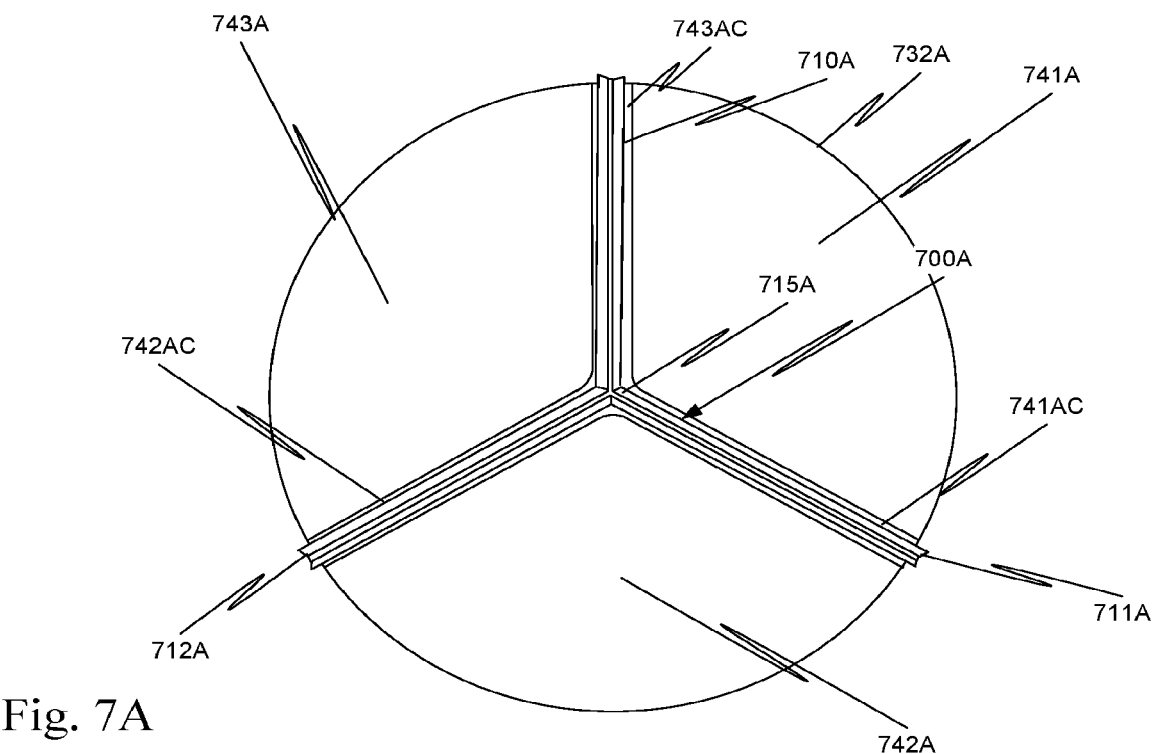
FIG. 7A is a bottom view of a portion of a surgical system that includes a main manipulator assembly on which are co-located three devices with a sterile channel pre-drape assembly installed.

FIG. 7A is a bottom view of a portion of a surgical system that includes a main manipulator assembly 732A supporting three co-located medical devices 741A, 742A, 743A. Each pair (741A, 742A), (742A, 743A), (743A, 741A) of adjacent devices of plurality of co-located medical devices 741A, 742A, 743A defines a channel, e.g., channels 741AC, 742AC, 743AC between that pair of co-located devices.

In the example of FIG. 7A, a plurality of legs of sterile channel pre-drape assembly 700A includes three legs 710A, 711A, 712A. Similar to the description of sterile channel pre-drape assembly 400, sterile channel pre-drape assembly 700A is a drape structure configured to be mounted in one or more channels 741AC, 742AC, 743AC formed by spacings between adjacent medical devices in plurality of co-located medical devices 741A, 741B, 741C.

The drape structure has a plurality of legs 710A, 711A, 712A that radiate from a common center region 715A. Each leg of plurality of legs 710A, 711A, 712A is configured to be inserted in one of one or more channels 741AC, 742AC, 743AC. Each leg of plurality of legs 710A, 711A, 712A has opposed exterior surfaces and sterile interior surfaces. The sterile interior surfaces of a pair of plurality of legs 710A, 711A, 712A creates a sterile channel in which a sterile drape pocket can be passed without comprising the sterility of the sterile drape pocket during individual draping of one of the plurality of co-located medical devices 741A, 742A, 743A.

Figure 7B:
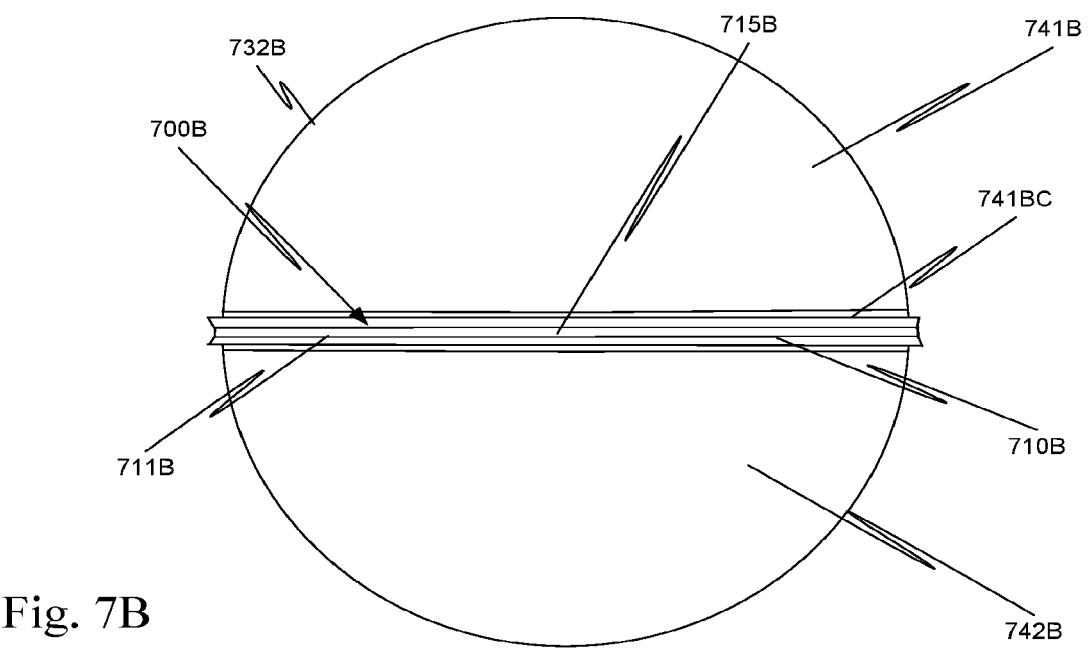
FIG. 7B is a bottom view of a portion of a surgical system that includes a main manipulator assembly on which are co-located two devices with a sterile channel pre-drape assembly installed.

FIG. 7B is a bottom view of a portion of a surgical system that includes a main manipulator assembly 732B on which are co-located two medical devices 741B, 742B. Each pair (741B, 742B) of adjacent devices of plurality of co-located medical devices 741B, 742B defines a channel, e.g., channel 741BC between the pair of co-located devices.

In the example of FIG. 7B, a plurality of legs of sterile channel pre-drape assembly 700B includes two legs 710B, 711B. Similar to the description of sterile channel pre-drape assembly 400, sterile channel pre-drape assembly 700B is a drape structure configured to be mounted in channel 741BC formed by the spacing between adjacent medical devices in plurality of co-located medical devices 741A, 741B.

The drape structure has a plurality of legs 710B, 711B that radiate from a common center region 715B. Each leg of plurality of legs 710B, 711B is configured to be inserted in channel 741AC. Each leg of plurality of legs 710B, 711B has opposed exterior surfaces and sterile interior surfaces. The sterile interior surfaces of plurality of legs 710B, 711B creates a sterile channel in which a sterile drape pocket can be passed without comprising the sterility of the sterile drape pocket during draping of one of the plurality of co-located medical devices 741B, 742B.

In view of this disclosure, a sterile channel pre-drape assembly can be used with a system having a plurality of N devices co-located on a common platform. Here, N is a positive integer number larger than or equal to two. Each pair of adjacent devices of the plurality of N co-located devices defines a channel between that pair of co-located devices, e.g., there is a plurality of N channels formed by the positioning of the plurality of N devices co-located on the common platform.

The sterile channel pre-drape assembly is a drape structure configured to be mounted in the plurality of N channels formed by the spacing between adjacent devices in the plurality of N co-located devices. The drape structure includes a plurality of N legs that radiate from a common center region. Each leg of the plurality of N legs is configured to be inserted in one of the plurality of N channels. Each leg of the plurality of N legs has opposed exterior surfaces and sterile interior surfaces. The sterile interior surfaces of a pair of the plurality of N legs creates a sterile channel in which a sterile drape pocket can be passed without comprising the sterility of the sterile drape pocket during individual draping of one of the plurality of N co-located devices.

Figures 8A, 8B:
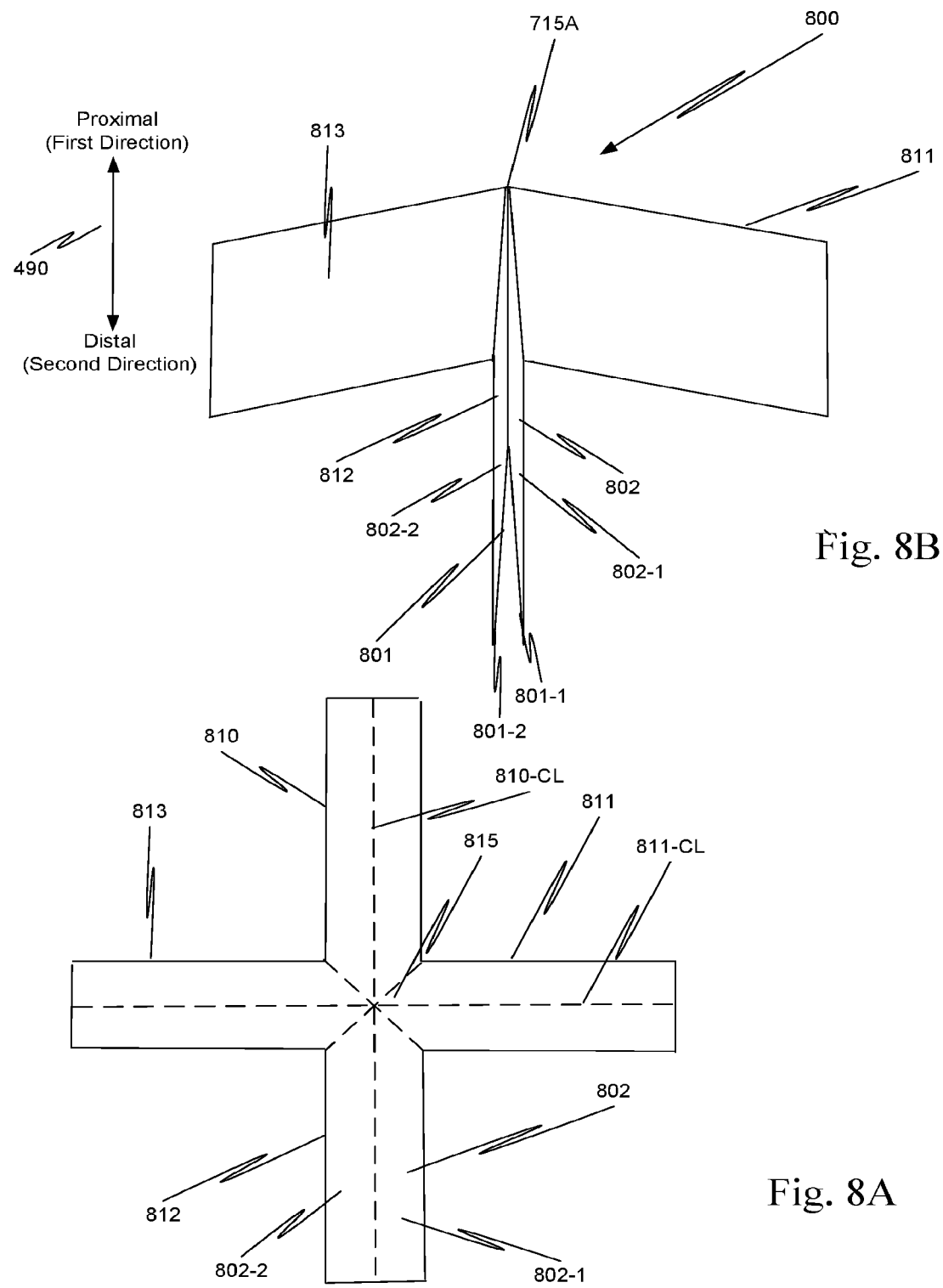
FIG. 8A is an illustration of a flat sheet of material that is folded to obtain a sterile channel pre-drape assembly.
FIG. 8B is an illustration of a sterile channel pre-drape assembly made by folding the flat sheet of material illustrated in FIG. 8A.

FIG. 8A is an illustration of a flat sheet of material that is folded to obtain the sterile channel pre-drape assembly 800

(FIG. 8B). FIGS. 8A and 8B are not drawn to scale and are not intended to illustrate any relative dimensions between the features of sterile channel pre-drape assembly 800.

In FIG. 8A, a single piece of material has the shape of a cross, i.e., the material has four legs 810, 811, 812, and 813. Legs 810 and 812 have a common center line 810-CL that intersects common center line 811-CL of legs 811 and 813 at a center of common center region 815. Here, a common center line means that the extended centerline of leg 810, for example, is the center line of leg 812.

Surface 802 of the single piece of material is treated as not being sterile, while the opposite side 801 of the single piece of material is sterile. The single piece of material, in one aspect, is semi-rigid, e.g., a synthetic material made of flashspun high-density polyethylene, molded urethane, a plastic sheet with shaping wires, etc. In one aspect, the flashspun high-density polyethylene is made by using 0.5 to 10 μm high density polyethylene fibers. The non-directional fibers are spun and bonded together by heat and pressure without binders. A synthetic material made of flashspun high-density polyethylene is sold under the U.S. registered trademark TYVEK® of E. I. du Pont de Nemours and Comany and is referred to as TYVEK® material.

When the material of FIG. 8A is folded on common center line 810-CL and common center line 811-CL, sterile channel pre-drape assembly 800 is formed. In FIG. 8A, the dashed lines represent fold lines.

The folding of the cross-shaped material of FIG. 8A creates a four-legged sterile channel pre-drape assembly 800, where each of legs 810 (not visible), 811, 812, and 813 radiate outward from common center region 815. Using leg 812 as an example of each of plurality of legs 810. 811, 812, 813, leg 812 has opposed exterior surfaces 802-1, 802-2 that are a portion of exterior surface 802. Leg 812 has sterile interior surfaces 801-1 and 801-2, which are bounded by exterior surfaces 802-1, 802-2. Sterile interior surfaces 801-1 and 801-2 are a portion of sterile surface 801 of sterile channel pre-drape assembly 800.

The distal end of leg 812 is open, and a distal edge of interior surface 801-1 is separated from a distal edge of interior surface 801-2 so that leg 812 is flared, e.g., has a triangular cross-section. The flaring of leg 812 facilities entering a sterile drape sleeve in a sterile channel bounded by sterile interior surfaces 801-1 and 801-2. While it not shown in FIGS. 8A and 8B, sterile channel pre-drape assembly 800 includes one or more attachment elements, e.g., magnetic disc, tape, to aid in installation of sterile channel pre-drape assembly 800 in deep non-sterile narrow openings between co-located medical devices.

Figure 9:
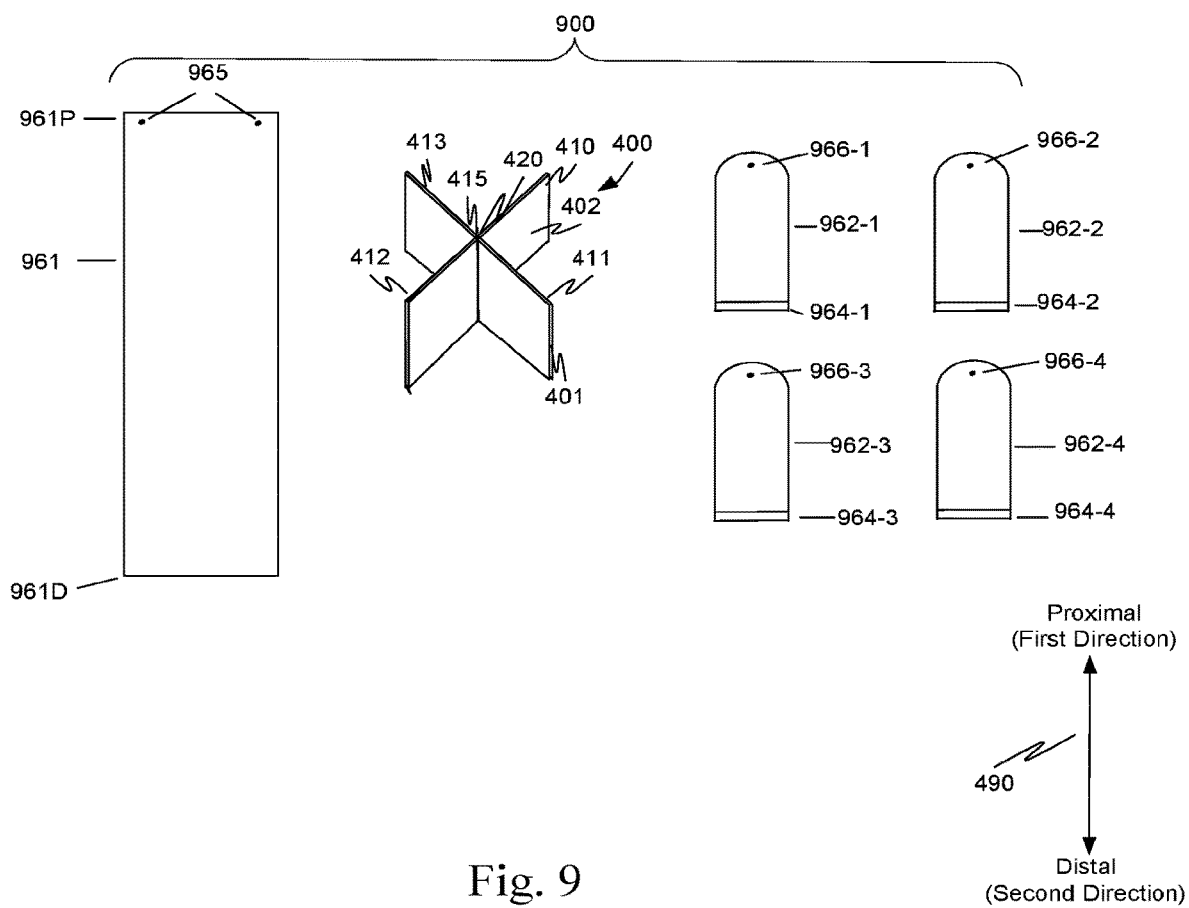
FIG. 9 is an illustration of an example of a sterile drape kit that includes a sterile arm drape sleeve, a sterile channel pre-drape assembly, and a plurality of sterile medical device sleeves.
Figure 10:
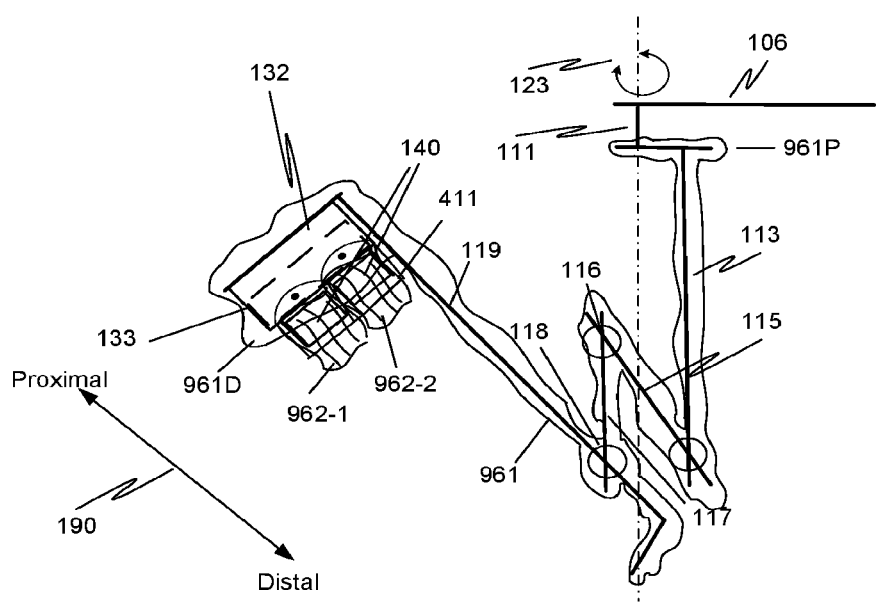
FIG. 10 is an illustration of a final phase in draping a patient side support system using the sterile drape kit of FIG. 9.

FIG. 9 is an illustration of an example of a sterile drape kit 900 for a medical device apparatus, such as patient side support system 110. Sterile drape kit 900 includes a sterile arm drape sleeve 961, a sterile channel pre-drape assembly 400, and a plurality of sterile medical device sleeves 962-1, 962-2, 962-3, 962-4. Unlike the prior art sterile drapes for patient side support system 110, each of the parts of sterile drape kit 900 does not require any complex manufacturing or bonding operations.

Sterile arm drape sleeve 961 is an example of a sterile manipulator arm assembly drape. Sterile arm drape sleeve 961 is open at both proximal end portion 961P and distal end portion 961D. Sterile arm drape sleeve 961 includes a sterile outer side—a first side—and an inner side—a second side, which is not treated as sterile. Sterile arm drape sleeve 961 includes a plurality of attachment elements 965 attached to proximal end portion 961P. Plurality of attachment elements 965 are selected to secure proximal end portion 961P of sterile arm drape sleeve 961 to a robotic arm, one link in a plurality of links, etc. Plurality of attachment elements 965 can be metal elements that are magnetically attached, grommets that fit over clips, tape, etc. Sterile arm drape sleeve 961 can also include plurality of assemblies 366 for managing and retaining sterile arm drape sleeve 961.

Sterile channel pre-drape assembly 400 is described above. Accordingly, the description of sterile channel pre-drape assembly 400 is not repeated here.

In this example, each of plurality of sterile medical device sleeves 962-1, 962-2, 962-3, 962-4, has the same configuration and so only sterile medical device sleeve 962-1 is considered in detail. Also, plurality of sterile medical device sleeves 962-1, 962-2, 962-3, 962-4 is an example of a plurality of sterile instrument manipulator sleeves. The description of parts of sterile medical device sleeve 962-1 is applicable to the corresponding parts, e.g., parts with the same base reference numeral, of the other sterile medical device sleeves. While in this example each of plurality of sterile medical device sleeves 962-1, 962-2, 962-3, 962-4, has a same configuration, this is illustrative only and is not intended to be limiting. Plurality of sterile medical device sleeves 962-1, 962-2, 962-3, 962-4, in general, is configured so that each of a plurality of co-located medical devices can be individually draped after sterile channel pre-drape assembly 400 is installed.

Sterile medical device sleeve 962-1 has an open proximal end and a distal end is attached to a mechanical interface element 964-1. Sterile medical device sleeves 962-1 includes a sterile outer side—a first side—and an inner side—a second side, which is not treated as sterile.

In one aspect, mechanical interface element 964-1 is a flexible membrane mechanical interface, such as that described in U.S. Patent Application Publication No. US 2011/0277776 A1. In another aspect, mechanical interface element 964-1 is an instrument sterile adapter, such as that described in U.S. Patent Application Publication No. US 2011/0277775 A1. Adjacent the open proximal end of sterile medical device sleeve 962-1 is one or more attachment elements 966-1, which are similar to the attachment elements described with respect to sterile arm drape sleeve 961.

To drape patient side support system 110 using sterile drape kit 900, sterile channel pre-drape assembly 400, and a plurality of sterile medical device sleeves 962-1, 962-2, 962-3, 962-4 are installed as described above with respect to FIGS. 6A to 6D, and so that description is not repeated here. The final phase in the draping, open proximal end portion 961P of sterile arm drape sleeve 961 is moved over links 119, 117, 115, and 113 of patient side support system 110 and attached to link 113 using plurality of attachment elements 965. Links 119, 117, 115, and 113 are an example of a manipulator arm assembly. Distal end portion 961D of sterile arm drape sleeve 961 extends over the collected ends of the co-located draped medical devices to finish off the draping process.

The slight extension of distal end portion 961D over the collected ends of plurality of sterile medical device sleeves 962-1, 962-2, 962-3, 962-4 covers over the remaining non-sterile slits and yet allow the entire collection of draped medical devices to rotate while maintaining sterility by sliding freely under the extended portion of sterile arm drape sleeve 961. Distal end portion 961D can also have an elastic band to help gather distal end portion 961D around the base of the rotating platform and hold it in place.

Typically, sterile channel pre-drape assembly 400 is left inside subsequent medical device drapes to provide additional abrasion resistance between a drape sleeve and/or a drape pocket and moving parts (e.g., telescoping arms). Further, by leaving sterile channel pre-drape assembly 400 in place the non-sterile center "ceiling" of the co-located medical device additionally remains covered to protect against any particulates from falling down to the sterile field.

Sterile channel pre-drape assembly 400 could also be referred to as a sterile abrasion shield assembly, because the pre-drape assembly described above has a dual functionality—assisting in draping and preventing abrasion of a drape during use of the draped part. The pre-drape assembly could be used as sterile abrasion shield assembly without necessarily making use of the draping assistance functionality if a co-located part were draped in a way different from that described herein. Further, the pre-drape and draping devices and assemblies disclosed herein optionally can be used to maintain cleanliness of medical devices. For example, in addition to, or instead of, maintaining a sterile field for a procedure, the pre-drape and drape assemblies can be used to protect the medical devices from contamination from a procedure in which the medical devices are used.

Hence, in one aspect, a sterile abrasion shield assembly is a structure configured to be mounted in one or more channels formed by spacings between adjacent medical devices in a plurality of co-located medical devices. The structure includes a plurality of legs. Each leg of the plurality of legs is configured to be inserted in one of the one or more channels. Also, each leg of the plurality of legs includes one or more exterior surfaces and one or more sterile interior surfaces. The one or more sterile interior surfaces of one or more legs of the plurality of legs create a sterile channel through which a sterile drape pocket can be passed without comprising sterility of the sterile drape pocket. In one aspect, the plurality of co-located medical devices is a plurality of surgical instrument manipulator assemblies. Also, in aspect, one or more of the plurality of legs is flared between a first end and a second end of the leg. Other aspect of the sterile abrasion shield are equivalent to the aspects of the sterile channel pre-drape assembly described above, and so are not repeated here, but are incorporated by reference to avoid a redundant description.

In the above description, both drape sleeves and drape pockets were considered. In the examples that utilized a drape sleeve, a drape pocket can be subsituted for the drape sleeve. Similarly, in the examples that utilized a drape pocket, a drape sleeve can be subsituted for the drape pocket.

As used herein, "first," "second," "third," etc. are adjectives used to distinguish between different components or elements. Thus, "first," "second," and "third" are not intended to imply any ordering of the components or elements or to imply any total number of components or elements.

The above description and the accompanying drawings that illustrate aspects and embodiments of the present inventions should not be taken as limiting—the claims define the protected inventions. Various mechanical, compositional, structural, electrical, and operational changes may be made without departing from the spirit and scope of this description and the claims. In some instances, well-known circuits, structures, and techniques have not been shown or described in detail to avoid obscuring inventive aspects.

Further, this description's terminology is not intended to limit the disclosure. For example, spatially relative terms—such as "beneath", "below", "lower", "above", "upper", "proximal", "distal", and the like—may be used to describe one element's or feature's relationship to another element or feature as illustrated in the figures. These spatially relative terms are intended to encompass different positions (i.e., locations) and orientations (i.e., rotational placements) of the device in use or operation in addition to the position and orientation shown in the figures. For example, if the device in the figures were turned over, elements described as "below" or "beneath" other elements or features would then be "above" or "over" the other elements or features. Thus, the exemplary term "below" can encompass both positions and orientations of above and below. The device may be otherwise oriented (rotated 90 degrees or at other orientations) and the spatially relative descriptors used herein interpreted accordingly. Likewise, descriptions of movement along and around various axes include various special device positions and orientations.

The singular forms "a", "an", and "the" are intended to include the plural forms as well, unless the context indicates otherwise. The terms "comprises", "comprising", "includes", and the like specify the presence of stated features, steps, operations, elements, and/or components but do not preclude the presence or addition of one or more other features, steps, operations, elements, components, and/or groups. Components described as coupled may be electrically or mechanically directly coupled, or they may be indirectly coupled via one or more intermediate components.

All examples and illustrative references are non-limiting and should not be used to limit the claims to specific implementations and embodiments described herein and their equivalents. Any headings are solely for formatting and should not be used to limit the subject matter in any way, because text under one heading may cross reference or apply to text under one or more headings. Finally, in view of this disclosure, particular features described in relation to one aspect or embodiment may be applied to other disclosed inventive aspects or embodiments, even though not specifically shown in the drawings or described in the text.

Embodiments described above illustrate but do not limit the disclosure. It should also be understood that numerous modifications and variations are possible in accordance with the principles of the present disclosure. For example, in many aspects the devices described herein are used as single-port devices; i.e., all components necessary to complete a surgical procedure enter the body via a single entry port. In some aspects, however, multiple devices and ports may be used.

I claim:

1. An apparatus comprising:
a sterile channel pre-drape assembly comprising a plurality of legs radiating in differing radial directions from a common center region, each of the plurality of legs comprising a pair of opposing and facing sterile interior surfaces and a pair of oppositely facing outer surfaces, wherein the pair of sterile interior surfaces defines a sterile channel,
wherein the interior and outer surfaces of each of the plurality of legs extend generally along a proximal-distal direction that is perpendicular to the differing radial directions; and
a sterile drape sleeve extending between an open proximal end and a distal end, the open proximal end of the sterile drape sleeve surrounded by wall portions of the sleeve,
wherein the wall portions of the sleeve are configured to be received in two sterile channels of a pair of adjacent legs of the plurality of legs of the sterile channel pre-drape assembly, and wherein, with the wall portions of the sterile drape sleeve received in the two sterile channels, the sterile drape sleeve extends distally from the sterile channel pre-drape assembly.

2. The apparatus of claim 1, further comprising:

an attachment element coupled to the sterile channel pre-drape assembly and in a position such that each of the plurality of legs is open to receive wall portions of a sterile drape sleeve in the channels defined by the plurality of legs.

3. The apparatus of claim 1:

wherein in the attached state of the sterile channel pre-drape assembly to the attachment element, each of the plurality of legs is positioned in a respective space between adjacent instrument manipulator assemblies such that respective outer surfaces of each leg is adjacent a respective one of the adjacent instrument manipulator assemblies.

4. The apparatus of claim 1, wherein the attachment element is affixed to the sterile channel pre-drape assembly at the common center region.

5. The apparatus of claim 1, wherein in an attached state of the sterile channel pre-drape assembly to the attachment element, the sterile channels of the sterile channel pre-drape assembly are open to receive a plurality of sterile drape sleeves in differing pairs of the sterile channels.

6. The apparatus of claim 1, further comprising:

a plurality of sterile drape sleeves, each of the plurality of sterile drape sleeves configured to individually drape one or more of a plurality of co-located instrument manipulator assemblies in a position of each sterile drape sleeve received in two sterile channels of differing pairs of adjacent legs of the plurality of legs of the sterile channel pre-drape assembly in the attached state of the sterile channel pre-drape assembly to a manipulator portion of the surgical system.

7. The apparatus of claim 1, wherein each of one or more of the plurality of legs comprises a first closed end and a second open end, wherein the interior surfaces of each channel flare outwardly away from each other in a direction from the first end to the second end.

8. The apparatus of claim 1, the sterile drape sleeve further comprising:

an instrument sterile adapter attached to the distal end of the sterile drape sleeve.

9. The apparatus of claim 1, the sterile drape sleeve further comprising:

a flexible membrane mechanical interface attached to the distal end of the sterile drape sleeve.

10. The apparatus of claim 1, wherein the plurality of legs comprises four legs radiating from the common center region.

11. The apparatus of claim 1, wherein each leg comprises a trapezoidal cross section in a plane parallel to a longitudinal axis of the sterile channel pre-drape assembly, the longitudinal axis passing through the common center region.

12. The apparatus of claim 1, wherein each of the plurality of legs comprises a folded sheet of material defining the interior and outer surfaces.

13. The apparatus of claim 1, wherein the plurality of legs radiate in differing directions from the common center region.

14. The apparatus of claim 1, wherein an angle between each pair of adjacent legs of the plurality of legs is uniform.

* * * * *

UNITED STATES PATENT AND TRADEMARK OFFICE
CERTIFICATE OF CORRECTION

PATENT NO. : 12,279,847 B2  
APPLICATION NO. : 16/185113  
DATED : April 22, 2025  
INVENTOR(S) : Humphrey W. Chow Page 1 of 1

It is certified that error appears in the above-identified patent and that said Letters Patent is hereby corrected as shown below:

In the Claims

Column 19, Claim 3, Line 11, delete "claim 1" and add --claim 2--.

Column 19, Claim 4, Line 19, delete "claim 1" and add --claim 2--.

Column 19, Claim 5, Line 22, delete "claim 1" and add --claim 2--.

Column 19, Claim 6, Line 27, delete "claim 1" and add --claim 2--.

Signed and Sealed this  
Sixteenth Day of September, 2025

Coke Morgan Stewart  
*Acting Director of the United States Patent and Trademark Office*